United States Patent
Hay et al.

(10) Patent No.: US 7,389,694 B1
(45) Date of Patent: Jun. 24, 2008

(54) RAIL INSPECTION SYSTEM

(76) Inventors: Thomas R. Hay, 317H Rex Pl., Madeira Beach, FL (US) 33708-1938; Robert Hay, 317H Rex Pl., Madeira Beach, FL (US) 33708-1938; Joseph L. Rose, 2465 Hickory Hill Dr., State College, PA (US) 16803

(*) Notice: Subject to any disclaimer, the term of this patent is extended or adjusted under 35 U.S.C. 154(b) by 148 days.

(21) Appl. No.: 11/375,083

(22) Filed: Mar. 14, 2006

(51) Int. Cl.
*G01N 29/04* (2006.01)

(52) U.S. Cl. .................. 73/635; 73/600; 73/636; 73/641; 73/644

(58) Field of Classification Search .............. 73/596, 73/622, 624, 628, 599, 600, 602, 643, 655, 73/635, 636, 639, 641, 644
See application file for complete search history.

(56) References Cited

U.S. PATENT DOCUMENTS

| | | | | |
|---|---|---|---|---|
| 4,738,501 A | * | 4/1988 | Sunagawa et al. | 385/7 |
| 5,150,437 A | * | 9/1992 | Gfeller | 385/7 |
| 5,418,866 A | * | 5/1995 | Chu | 385/7 |
| 5,852,702 A | * | 12/1998 | Nishida et al. | 385/130 |
| 6,356,299 B1 | * | 3/2002 | Trosino et al. | 348/128 |
| 6,360,609 B1 | * | 3/2002 | Wooh | 73/602 |
| 6,799,466 B2 | * | 10/2004 | Chinn | 73/622 |
| 6,810,743 B2 | * | 11/2004 | Madaras et al. | 73/598 |
| 2004/0263624 A1 | * | 12/2004 | Nejikovsky et al. | 348/148 |

* cited by examiner

*Primary Examiner*—Hezron E. Williams
*Assistant Examiner*—Jacques M. Saint-Surin
(74) *Attorney, Agent, or Firm*—Edward P Dutkiewicz

(57) ABSTRACT

An apparatus rides along a rail of a railroad track. A transmitter transmits ultrasonic guided waves bidirectionally along the rail while the apparatus and transmitter are moving along the railroad track. A sensor detects flaws in response to the transmitted ultrasonic guided waves while the apparatus, transmitter and sensor are moving along the railroad track. An electronic coupler operatively couples the sensor to monitoring equipment.

1 Claim, 3 Drawing Sheets

FIG 6
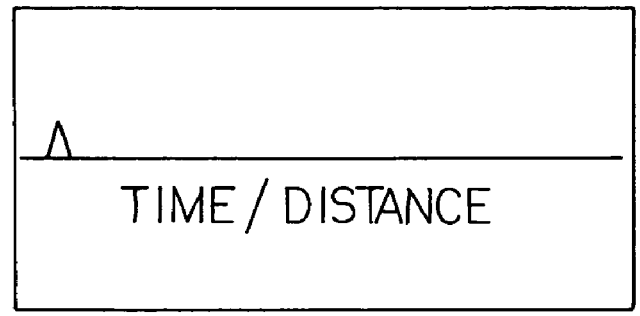
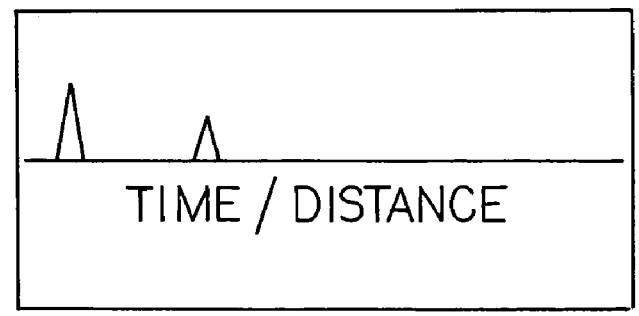
FIG 7

RAIL INSPECTION SYSTEM

BACKGROUND OF THE INVENTION

1. Field of the Invention

The present invention relates to a rail inspection system and more particularly pertains to bidirectionally evaluating and detecting flaws in railroad tracks.

2. Description of the Prior Art

The use of rail inspection systems of known designs and configurations is known in the prior art. More specifically, rail inspection systems of known designs and configurations previously devised and utilized for the purpose of detecting flaws in railroad tracks are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 6,262,572 issued Jul. 17, 2001, to Wojnarowski et al. discloses an electromagnetic system for railroad track crack detection and traction enhancement. U.S. Pat. No. 5,386,727 issued Feb. 7, 1995, to Earle discloses a dynamic rail longitudinal stress measuring system. Finally, U.S. Pat. No. 4,468,966 issued Sep. 4, 1984 to Bradshaw discloses a railroad track inspection car.

While these devices fulfill their respective, particular objectives and requirements, the aforementioned patents do not describe a rail inspection system that allows bidirectionally evaluating and detecting flaws in railroad tracks.

In this respect, the rail inspection system according to the present invention substantially departs from the conventional concepts and designs of the prior art, and in doing so provides an apparatus primarily developed for the purpose of bidirectionally evaluating and detecting flaws in railroad tracks.

Therefore, it can be appreciated that there exists a continuing need for a new and improved rail inspection system which can be used for bidirectionally evaluating and detecting flaws in railroad tracks. In this regard, the present invention substantially fulfills this need.

SUMMARY OF THE INVENTION

In view of the foregoing disadvantages inherent in the known types of rail inspection systems of known designs and configurations now present in the prior art, the present invention provides an improved rail inspection system. As such, the general purpose of the present invention, which will be described subsequently in greater detail, is to provide a new and improved rail inspection system and method which has all the advantages of the prior art and none of the disadvantages.

To attain this, the present invention essentially comprises a portable direct rail inspection system which allows a user to bidirectionally evaluate and detect flaws in railroad tracks. First provided is a vehicle. The vehicle has an undercarriage and is adapted to ride along a rail of a railroad track. An apparatus is next provided. The apparatus is coupled by an apparatus mount to the guide wheel of the undercarriage. A mounting pin aperture is provided through the apparatus mount.

Next provided is a downwardly displaced arm. The arm has an upper end and a lower end. A centrally located mounting pin aperture is provided through the upper end. A wheel axle hole is provided through the lower end. A mounting pin fabricated of rigid material is next provided. The mounting pin pivotably couples the downwardly displaced arm and the apparatus mount.

Next provided are a first wheel and a second wheel. Each wheel has an inner side and an outer side and a thickness there between. The inner side of the first wheel has a flange of a first diameter to secure the apparatus on the rail. The outer side of the first wheel has a round track contact surface of a second diameter.

A first axle fabricated of rigid material is next provided. The first axle couples the first wheel to the downwardly displaced arm and a sensor mounting bracket. The sensor mounting bracket has an inner side and an outer side and a thickness there between. The sensor mounting bracket also has a forward end and a rearward end with an extent there between. The sensor mounting bracket also has a first axle aperture on the forward end to allow coupling the sensor mounting bracket to the first axle. The sensor mounting bracket also has a second axle aperture on the rearward end to allow coupling of the sensor mounting bracket to a second axle. The second axle is fabricated of rigid material and is adapted to couple the second wheel to the sensor mounting bracket.

A transmitter is next provided. The transmitter is adapted to transmit ultrasonic guided waves selected from the class of ultrasonic guided waves including Lamb waves, Stoneley waves, Rayleigh waves, Sezawa waves and Love waves. The waves are transmitted bidirectionally along the rail while the vehicle, apparatus, and transmitter are moving along the railroad track.

Next a sensor is provided. The sensor is adapted to detect flaws in response to the transmitted ultrasonic guided waves while the vehicle, apparatus, transmitter and sensor are moving along the railroad track. Lastly, an electronic coupler is provided. The electronic coupler operatively couples the sensor to monitoring equipment.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved rail inspection system which has all of the advantages of the prior art rail inspection systems of known designs and configurations and none of the disadvantages.

It is another object of the present invention to provide a new and improved rail inspection system which may be easily and efficiently manufactured and marketed.

It is further object of the present invention to provide a new and improved rail inspection system which is of durable and reliable constructions.

An even further object of the present invention is to provide a new and improved rail inspection system which is susceptible of a low cost of manufacture with regard to both materials and labor, and which accordingly is then susceptible of low prices of sale to the consuming public, thereby making such rail inspection system economically available.

Even still another object of the present invention is to provide a rail inspection system for bidirectionally evaluating and detecting flaws in railroad tracks.

Lastly, it is an object of the present invention to provide a new and improved apparatus which rides along a rail of a railroad track having a transmitter which transmits ultrasonic guided waves bidirectionally along the rail while the apparatus and transmitter are moving along the railroad track, a sensor which detects flaws in response to the transmitted ultrasonic guided waves while the apparatus, transmitter and sensor are moving along the railroad track, and an electronic coupler which operatively couples the sensor to monitoring equipment.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIGS. 4 through 7 are schematic illustrations of the sensing of a defect in a rail by the present invention.

The same reference numerals refer to the same parts throughout the various Figures.

DESCRIPTION OF THE PREFERRED EMBODIMENT

Figure 1:
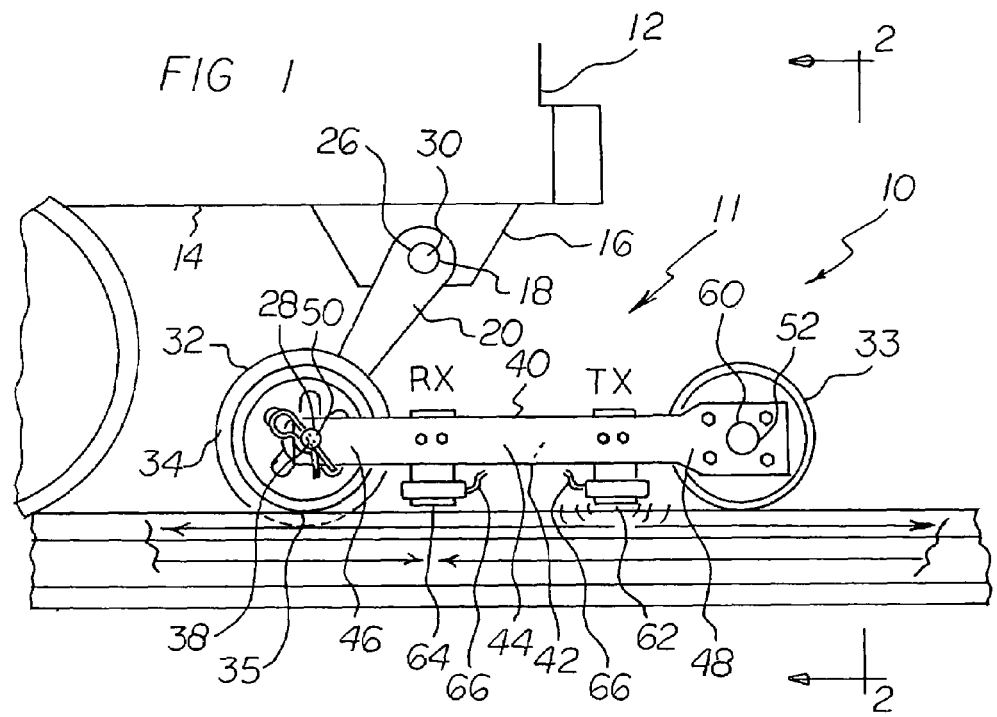
FIG. 1 is a side elevational view of a portable direct sensor attachment system constructed in accordance with the principles of the present invention.
Figure 2:
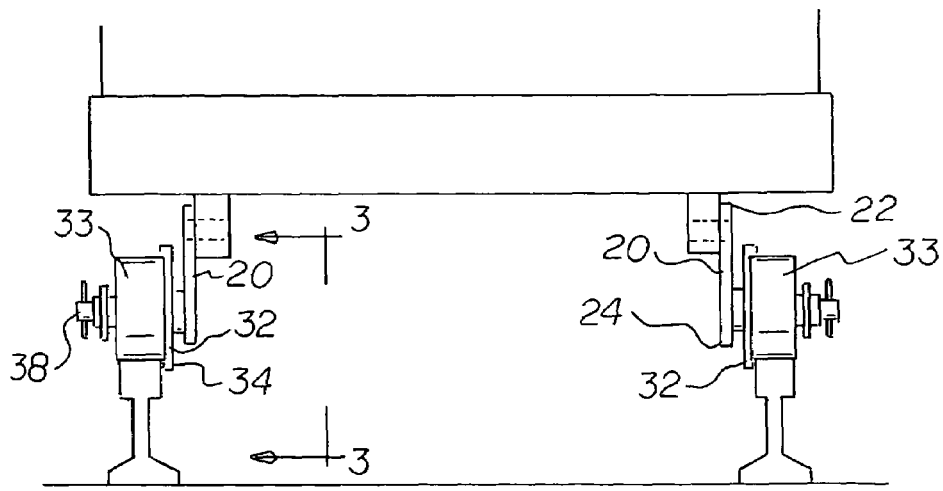
FIG. 2 is a front elevational view taken along line 2-2 of FIG. 1.
Figure 3:
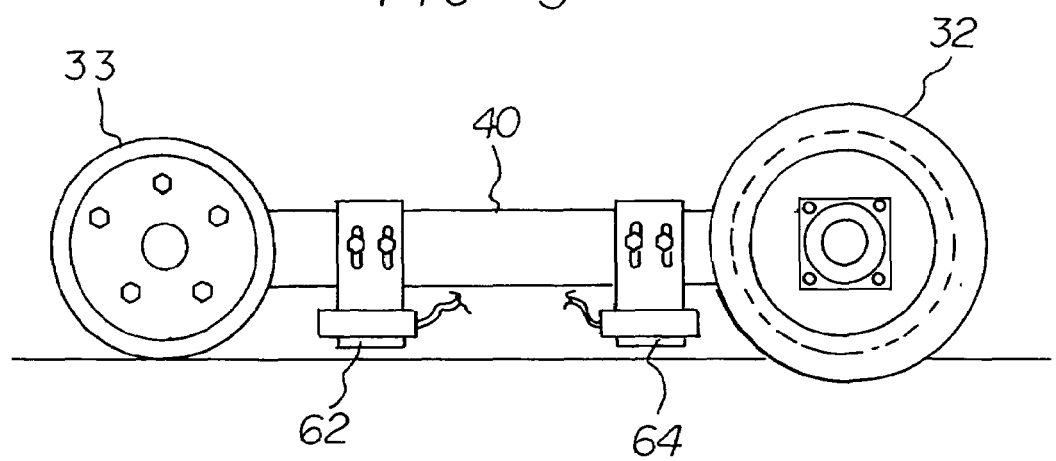
FIG. 3 is a side elevational view taken along line 3-3 of FIG. 2.

With reference now to the drawings, and in particular to FIG. 1 thereof, the preferred embodiment of the new and improved rail inspection system embodying the principles and concepts of the present invention and generally designated by the reference numeral 10 will be described.

The present invention, the rail inspection system 10 is comprised of a plurality of components. Such components in their broadest context include a vehicle, a transmitter, a sensor and an electronic coupler. Such components are individually configured and correlated with respect to each other so as to attain the desired objective.

The portable direct rail inspection system allows a user to bidirectionally evaluate and detect flaws in railroad tracks.

First provided is a vehicle 12. The vehicle has an undercarriage 14 and is adapted to ride along a rail of a railroad track.

An apparatus 11 is next provided. The apparatus is coupled by an apparatus mount 16 to the guide wheel of the undercarriage. A mounting pin aperture is provided through the apparatus mount.

Next provided is a downwardly displaced arm 20. The arm has an upper end 22 and a lower end 24. A centrally located mounting pin aperture 26 is provided through the upper end. A wheel axle hole 28 is provided through the lower end.

A mounting pin 30 fabricated of rigid material is next provided. The mounting pin pivotably couples the downwardly displaced arm and the apparatus mount.

Next provided are a first wheel 32 and a second wheel 33. Each wheel has an inner side and an outer side and a thickness there between. The inner side of the first wheel has a flange 34 of a first diameter to secure the apparatus on the rail. The outer side of the first wheel has a round track contact surface 35 of a second diameter.

A first axle 38 fabricated of rigid material is next provided. The first axle couples the first wheel to the downwardly displaced arm and a sensor mounting bracket 40. The sensor mounting bracket has an inner side 42 and an outer side 44 and a thickness there between. The sensor mounting bracket also has a forward end 46 and a rearward end 48 with an extent there between. The sensor mounting bracket also has a first axle aperture 50 on the forward end to allow coupling the sensor mounting bracket to the first axle. The sensor mounting bracket also has a second axle aperture 52 on the rearward end to allow coupling of the sensor mounting bracket to a second axle 60. The second axle is fabricated of rigid material and is adapted to couple the second wheel to the sensor mounting bracket.

A transmitter 62 is next provided. The transmitter is adapted to transmit ultrasonic guided waves selected from the class of ultrasonic guided waves including Lamb waves, Stoneley waves, Rayleigh waves, Sezawa waves and Love waves. The waves are transmitted bidirectionally along the rail while the vehicle, apparatus, and transmitter are moving along the railroad track.

Next a sensor 64 is provided. The sensor is adapted to detect flaws in response to the transmitted ultrasonic guided waves while the vehicle, apparatus, transmitter and sensor are moving along the railroad track.

Lastly, an electronic coupler 66 is provided. The electronic coupler operatively couples the sensor to monitoring equipment 68.

This invention is a new ultrasonic guided wave inspection concept for rails. It applies to the use of an ultrasonic inspection approach that involves four major characteristics: 1) an ultrasonic wave propagation mode that launches energy longitudinally, parallel to the rail, compared to conventional methods that inspect only directly under the insertion point or on a line at a specified angle below the insertion point; 2) an ultrasonic transduction method that launches ultrasonic energy bi-directionally from the insertion point, compared to conventional methods that emit unidirectionally; and 3) an ultrasonic wave propagation mode that focuses energy in the rail head for detection of transverse defects in the head including gauge corner cracks, transverse/compound fissure, and detail fractures.

The rail inspection requirement also involves inspection irregular surfaces at high speeds with a high probability of detection. The innovation disclosed herein describes the application of the characteristics identified above to address this requirement for reliable inspection under fluctuating geometry at high speed.

While conventional rail inspection technology uses pulse-echo or through-transmission methods for defect detection, the present invention uses both to fully exploit the two characteristics of the inspection procedure introduced above. The use of a dual transducer assembly is implemented innovatively to exploit the ability to inspect in front and behind the excitation source with the ultrasonic transduction method that launches ultrasonic waves bi-directionally from the insertion point and to provide continuous calibration to accommodate rapid geometric fluctuation.

Rail is conventionally inspected on a routine basis using ultrasonic bulk waves that are generated on the top surface of the rail for head, web and base inspection. The ultrasonic waves are introduced into the rail using piezoelectric transducers contained inside a rubber wheel that travels at high speeds along the top surface of the rail. The ultrasonic waves travel from the top of the rail toward the bottom of the rail. If a discontinuity is present in the rail, the ultrasonic wave will be reflected back toward the transducers. Each transducer in the wheel emits a pulse of ultrasound into the rail and then operates as a receiver as it waits for reflections from rail discontinuities. This single transducer mode is referred to as pulse-echo.

The defining characteristics of conventional bulk wave rail inspection are: 1) It operates in pulse-echo mode only; 2) It searches direction underneath the wheel probe for defects and cannot locate defects in front or behind the wheel; 3) The inspection reference point is the top of the rail. Defects are located relative to the top of, through the head, web and base of the rail; 4) Reflections from rail defects are static which in this context means that their relative position to the transducers cannot be exploited for rail defect location information and verification purposes; and 5) This inspection method can be significantly limited by the presence of surface conditions such as shelling.

Guided waves as used in the present invention are another family of wave modes that may be used to inspect structures with well-defined boundaries including rail, pipe, rod, plates, and layered media. Guided waves include Lamb waves, Stoneley waves, Rayleigh waves, Sezawa waves and Love waves. Unlike bulk wave inspection, guided waves search for rail defects beyond the area located directly underneath the transducers. In this context, it is not limited to a point-by-point inspection.

The transducer and data acquisition procedure of the present invention are presented herein. The figures illustrate two electromagnetic acoustic transducers (EMATs) are used. The transmitter TX is located on the left and the receiver RX is locate don the right. The transmitter TX inputs a pulse into the rail that travels in front (to the right) and behind (to the left) of the transmitter TX. In this configuration, and as shown by the arrows of FIG. 1, there are three signals of interest:

1) Direct through-transmission signal. The direct through transmission signal travels a short distance between the TX and RX. Note that the distance between the TX and RX is fixed. Therefore, the arrival time and distance the wave travels is fixed. The signal is acquired in through-transmission mode. Amplitude variations of the direct signal are used for rail discontinuity detection and inspection redundancy.

2) Guided waves traveling in the forward direction: The direct through transmission signal travels beyond the rX and searching and rail distoninuities. In this pseudo pulse-echo mode, reflections are relative to the position of the EMATs. Since the EMATs are moving forward, a reflection's arrival time and distance will also move forward. This translates into shorter arrival times and distances as the EMATs approach the discontinuities. The forward moving reflections are used for discontinuity verification and inspection redundancy.

3) Guided waves traveling in the backward direction: Since the TX emits waves behind the EMATs, it becomes possible to detect discontinuities behind the EMATs. IN this pseudo pulse-echo mode, reflections are again relative to the position of the EMATs. Since the EMATs are moving backward, a reflection's arrival time and distance will also move backward or further away from the TX-RX pair. This translates into longer arrival times and distances as the EMATs pull away from the discontinuities. The backward moving reflections are used for discontinuity verification and inspection redundancy.

These features differentiate the invention from existing guided wave rail inspection techniques and published technologies that operate only in pulse-echo mode, or only in through-transmission mode, or that acquire data in a static configuration meaning that neither the rail nor transducers are in motion.

In the present invention, the carriage is pulled along the rail by a maintenance or inspection vehicle. The transmitting transducer generates guided waves in both directions. The receiving transducer picks up direct through transmission pulse from transmitter and pulse-echo reflections from discontinuities in front and behind the pair of transducers. As the transducers move forward, the reflection from this rail discontinuity will register further out in distance and time. As the transducers move forward, the reflection from this rail discontinuity will register nearer in time and distance.

The direct signal is between the transmitting and receiving transducers in through transmission mode. Since the transducer separation distance is fixed the direct signal will always be received at the same location. FIG. 1 shows the reflected pulse from the rail behind the transducers. This reflection will move toward the right as the transducers approach the rail end. Again FIG. 1 shows the reflected pulse from the rail and in front of the transducers. This reflection will move toward the left as the transducers approach the rail end.

In the prior art, the bi-directionality of guided waves has been cited as a disadvantage since reflections from structural discontinuities in front of the sensors can be confused with those from behind the sensors. Consider a sensor on a pipe that emits guided waves in front and behind the sensors. Since the pipe is stationary, ultrasonic reflections will not move relative to the sensing array their arrival time and distance will remain fixed. The prior art addresses canceling out the wave propagation in one direction. By moving the transducers over the inspected structure or the inspected structure under the EMATs, reflections from discontinuities become dynamic. The dynamic nature of these defects is exploited in the present invention which improves inspection performance in terms of data redundancy. The following sequence shown in FIGS. 4-7 is used to explain how the dynamic nature of rail discontinuity reflections are used for improved inspection performance.

The purposeful implementation of the direct through-transmission signal amplitude for defect sizing and defect detection redundancy is also claimed as part of the present invention. For defect sizing purposes, the amplitude ratio of the maximum amplitude of the direct signal to that of a rail defect reflection is claimed as one part of the purposeful implementation. Monitoring the direct signal amplitude for data redundancy is also claimed in the invention. In this scenario, a rail defect in between the TX and RX will become apparent in the amplitude and shape of the direct signal.

Theoretical models and experimental validation of the model identified the guided wave modes, frequencies, and wavelength required for optimized transverse defect detection in the rail head. The present invention is the first technology designed exclusively for defect detection in the rail head based on input from physical elastodynamic and FEM modes validated through experiment. The technology is also capable of detecting defects below shelling on the rail surface which may be difficult with other conventional rail inspection technology.

Figure 4:
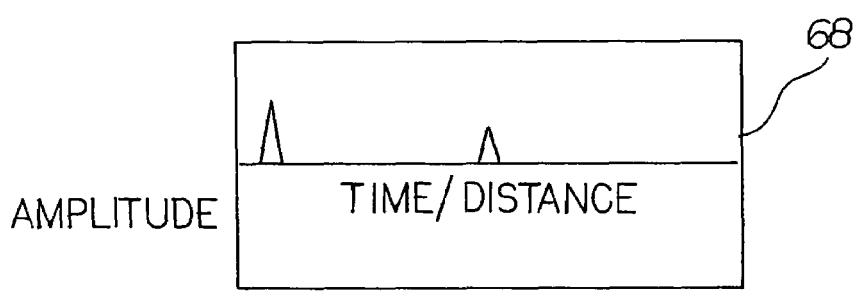
Figure 5:
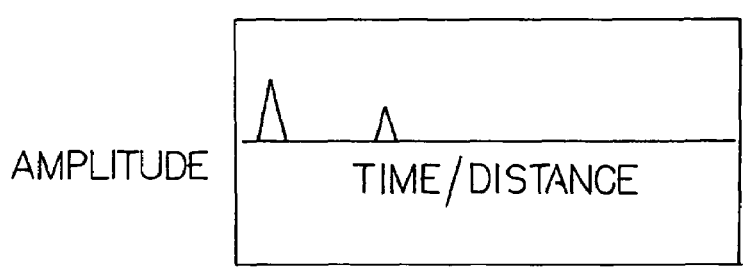

FIGS. 4 through 7 provide an explanation of bidirectionality and how it is purposefully used to observe the same rail discontinuities in front and behind the EMAT pairs. In FIG. 4, the arrival time and distance of the direct signal remains constant and the arrival time and distance of the discontinuity reflection is received. In FIG. 5, the arrival time and distance of the direct signal remains constant and as the EMATs approach the discontinuity, the arrival time and distance decrease. In FIG. 6, when the discontinuity is in between the EMATs, it will experience a change in amplitude and the discontinuity reflect is lost when it is located in between EMATs. In FIG. 7, once the EMATs pass the defect, the signal returns. The discontinuity reflection from behind the sensor is acquired.

From the above descriptions, it can be seen that the present invention involves:

1) Ultrasonic guided wave technology capable of detecting transverse defects in the head underneath surface damage including shelling;

2) Ultrasonic frequency range specifically for defect detection in the rail head;

3) Purposeful implementation of guided wave bidirectionality for rail defect detection, location, and redundancy;

4) Dynamic rail inspection with a moving vehicle and with moving guided waves; and 5) The use of a dual transducers assembly implemented innovatively to exploit the ability to inspect in front and behind the excitation source with the ultrasonic transduction method that launches ultrasonic waves bi-directionally from the insertion point and to provide continuous calibration to accommodate rapid geometric fluctuation.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A portable direct rail inspection system for allowing a user to bidirectionally evaluate and detect flaws in railroad tracks comprising, in combination:

a vehicle having an undercarriage with a guide wheel and being adapted to ride along a rail of a railroad track;

an apparatus coupled by an apparatus mount to the guide wheel of the undercarriage, the apparatus mount having a mounting pin aperture there through;

a downwardly displaced arm having an upper end and a lower end, the upper end having a centrally located mounting pin aperture there through and the lower end having a wheel axle hole there through;

a mounting pin fabricated of rigid material and pivotably coupling the downwardly displaced arm and the apparatus mount;

a first wheel and a second wheel, each wheel having an inner side and an outer side and a thickness there between, the inner side of the first wheel having a flange of a first diameter to secure the apparatus on the rail and the outer side having a round track contact surface of a second diameter;

a first axle fabricated of rigid material to couple the first wheel to the downwardly displaced arm and a sensor mounting bracket, the sensor mounting bracket having an inner side and an outer side and a thickness there between, and a forward end and a rearward end with an extent there between, the sensor mounting bracket also having a first axle aperture on the forward end to allow coupling the sensor mounting bracket to the first axle, the sensor mounting bracket also having a second axle aperture on the rearward end to allow coupling of the sensor mounting bracket to a second axle fabricated of rigid material, the second axle adapted to couple the second wheel to the sensor mounting bracket;

a transmitter adapted to transmit ultrasonic guided waves selected from the class of ultrasonic guided waves including Lamb waves, Rayleigh waves, Sezawa waves and Love waves, bidirectionally along the rail while the vehicle, apparatus, and transmitter are moving along the railroad track;

a sensor adapted to detect flaws in response to the transmitted ultrasonic guided waves while the vehicle, apparatus, transmitter and sensor are moving along the railroad track; and an electronic coupler for operatively coupling the sensor to monitoring equipment.

\* \* \* \* \*